(12) United States Patent
Rottenberg et al.

(10) Patent No.: US 8,721,675 B2
(45) Date of Patent: *May 13, 2014

(54) LUMEN REENTRY DEVICES AND METHODS

(75) Inventors: Dan Rottenberg, Haifa (IL); Abi Zakay, Zichron Yacov (IL)

(73) Assignee: Boston Scientific Limited, Christ Church (BB)

( * ) Notice: Subject to any disclaimer, the term of this patent is extended or adjusted under 35 U.S.C. 154(b) by 0 days.

This patent is subject to a terminal disclaimer.

(21) Appl. No.: 13/594,019

(22) Filed: Aug. 24, 2012

(65) Prior Publication Data

US 2012/0323269 A1 Dec. 20, 2012

Related U.S. Application Data

(63) Continuation of application No. 12/058,714, filed on Mar. 30, 2008, now Pat. No. 8,257,382.

(60) Provisional application No. 60/920,561, filed on Mar. 29, 2007, provisional application No. 60/994,732, filed on Sep. 24, 2007, provisional application No. 60/997,099, filed on Oct. 2, 2007.

(51) Int. Cl.
*A61M 25/10* (2013.01)

(52) U.S. Cl.
USPC .......................................................... 606/194

(58) Field of Classification Search
USPC .................. 600/184, 207; 604/96.01, 101.01, 604/101.03, 101.05; 606/190–192, 194, 606/198
See application file for complete search history.

(56) References Cited

U.S. PATENT DOCUMENTS

| | | | |
|---|---|---|---|
| 3,833,004 | A | 9/1974 | Blake |
| 4,271,839 | A | 6/1981 | Fogarty |
| 4,299,226 | A | 11/1981 | Banka |
| 4,630,609 | A | 12/1986 | Chin |
| 4,661,095 | A | 4/1987 | Taller et al. |
| 4,758,221 | A | 7/1988 | Jureidini |

(Continued)

FOREIGN PATENT DOCUMENTS

| | | |
|---|---|---|
| EP | 0359489 A2 | 9/1990 |
| JP | 2005-58504 A | 3/2010 |
| WO | 0176678 A1 | 10/2001 |
| WO | 2007033052 A2 | 3/2007 |

OTHER PUBLICATIONS

Belli, Anna-Maria et al., "Peripheral Vascular Occlusions: Mechanical Recanalization with a Metal Laser Probe after Guide Wire Dissection" Radiology, vol. 176 No. 2, Aug. 1990, pp. 539-541.

(Continued)

*Primary Examiner* — Ryan Severson
(74) *Attorney, Agent, or Firm* — Seager, Tufte & Wickhem, LLC

(57) ABSTRACT

A device, such as for use with lumen reentry, including a catheter including a balloon disposed at a distal end thereof, the catheter being formed with a first lumen through the balloon for passing therethrough a guidewire and a second lumen for inflation and deflation of the balloon, the catheter and the balloon being sized and shaped for entry between two layers of a wall of a body lumen, wherein upon expansion of the balloon when placed between the layers, a distal portion of the first lumen that passes through the balloon is bent with respect to a portion of the first lumen proximal to the balloon and is directed towards the body lumen.

12 Claims, 11 Drawing Sheets

(56) References Cited

U.S. PATENT DOCUMENTS

| | | |
|---|---|---|
| 4,863,424 A | 9/1989 | Blake |
| 4,927,412 A | 5/1990 | Menasche |
| 4,976,710 A | 12/1990 | Mackin |
| 4,990,138 A | 2/1991 | Bacich et al. |
| 5,074,845 A | 12/1991 | Miraki |
| 5,092,848 A | 3/1992 | deCiutiis |
| 5,109,830 A | 5/1992 | Cho |
| 5,336,176 A | 8/1994 | Yoon |
| 5,423,846 A | 6/1995 | Fischell |
| 5,514,153 A | 5/1996 | Bonutti |
| 5,522,832 A | 6/1996 | Kugo et al. |
| 5,601,588 A | 2/1997 | Tonomura |
| 5,607,435 A | 3/1997 | Sachdeva |
| 5,628,761 A | 5/1997 | Rizik |
| 5,667,520 A | 9/1997 | Bonutti |
| 5,830,222 A | 11/1998 | Makower |
| 5,860,997 A | 1/1999 | Bonutti |
| 5,916,194 A | 6/1999 | Jacobsen et al. |
| 5,935,108 A | 8/1999 | Katoh et al. |
| 5,938,671 A | 8/1999 | Katoh et al. |
| 5,968,064 A | 10/1999 | Selmon et al. |
| 5,997,503 A | 12/1999 | Willis et al. |
| 6,010,449 A | 1/2000 | Selmon et al. |
| 6,068,638 A | 5/2000 | Makower |
| 6,120,516 A | 9/2000 | Selmon et al. |
| 6,159,225 A | 12/2000 | Makower |
| 6,190,353 B1 | 2/2001 | Makower et al. |
| 6,206,868 B1 | 3/2001 | Parodi |
| 6,217,527 B1 | 4/2001 | Selmon et al. |
| 6,217,549 B1 | 4/2001 | Selmon et al. |
| 6,221,049 B1 | 4/2001 | Selmon et al. |
| 6,231,546 B1 | 5/2001 | Milo et al. |
| 6,231,587 B1 | 5/2001 | Makower |
| 6,235,000 B1 | 5/2001 | Milo et al. |
| 6,241,667 B1 | 6/2001 | Vetter et al. |
| 6,261,304 B1 | 7/2001 | Hall et al. |
| 6,264,631 B1 | 7/2001 | Willis et al. |
| 6,283,951 B1 | 9/2001 | Flaherty et al. |
| 6,283,983 B1 | 9/2001 | Makower et al. |
| 6,302,875 B1 | 10/2001 | Makower et al. |
| 6,330,884 B1 | 12/2001 | Kim |
| 6,375,615 B1 | 4/2002 | Flaherty et al. |
| 6,387,119 B2 | 5/2002 | Wolf et al. |
| 6,398,798 B2 | 6/2002 | Selmon et al. |
| 6,423,032 B2 | 7/2002 | Parodi |
| 6,432,127 B1 | 8/2002 | Kim et al. |
| 6,464,665 B1 | 10/2002 | Heuser |
| 6,506,178 B1 | 1/2003 | Schubart et al. |
| 6,508,825 B1 | 1/2003 | Selmon et al. |
| 6,511,458 B2 | 1/2003 | Milo et al. |
| 6,514,217 B1 | 2/2003 | Selmon et al. |
| 6,519,225 B1 | 2/2003 | Angle et al. |
| 6,533,753 B1 | 3/2003 | Haarstad et al. |
| 6,544,230 B1 | 4/2003 | Flaherty et al. |
| 6,579,302 B2 | 6/2003 | Duerig et al. |
| 6,579,311 B1 | 6/2003 | Makower |
| 6,599,304 B1 | 7/2003 | Selmon et al. |
| 6,602,241 B2 | 8/2003 | Makower et al. |
| 6,613,081 B2 | 9/2003 | Kim et al. |
| 6,616,675 B1 | 9/2003 | Evard et al. |
| 6,632,184 B1 | 10/2003 | Truwit |
| 6,638,247 B1 | 10/2003 | Selmon et al. |
| 6,638,293 B1 | 10/2003 | Makower et al. |
| 6,655,386 B1 | 12/2003 | Makower et al. |
| 6,660,024 B1 | 12/2003 | Flaherty et al. |
| 6,663,577 B2 | 12/2003 | Jen et al. |
| 6,685,648 B2 | 2/2004 | Flaherty et al. |
| 6,694,983 B2 | 2/2004 | Wolf et al. |
| 6,709,444 B1 | 3/2004 | Makower |
| 6,719,725 B2 | 4/2004 | Milo et al. |
| 6,726,677 B1 | 4/2004 | Flaherty et al. |
| 6,746,464 B1 | 6/2004 | Makower |
| 6,916,307 B2 | 7/2005 | Willis et al. |
| 6,955,175 B2 | 10/2005 | Stevens et al. |
| 6,960,222 B2 | 11/2005 | Vo et al. |
| 6,979,290 B2 | 12/2005 | Mourlas et al. |
| 7,004,173 B2 | 2/2006 | Sparks et al. |
| 7,059,330 B1 | 6/2006 | Makower et al. |
| 7,094,230 B2 | 8/2006 | Flaherty et al. |
| 7,134,438 B2 | 11/2006 | Makower et al. |
| 7,159,592 B1 | 1/2007 | Makower et al. |
| 7,179,270 B2 | 2/2007 | Makower |
| 7,229,421 B2 | 6/2007 | Jen et al. |
| 7,303,571 B2 | 12/2007 | Makower et al. |
| 7,316,655 B2 | 1/2008 | Garibotto et al. |
| 7,357,794 B2 | 4/2008 | Makower et al. |
| 7,407,506 B2 | 8/2008 | Makower |
| 7,534,204 B2 | 5/2009 | Starksen et al. |
| 7,637,870 B2 | 12/2009 | Flaherty et al. |
| 7,648,517 B2 | 1/2010 | Makower et al. |
| 7,670,329 B2 | 3/2010 | Flaherty et al. |
| 7,729,738 B2 | 6/2010 | Flaherty et al. |
| 7,740,623 B2 | 6/2010 | Nayak et al. |
| 7,846,172 B2 | 12/2010 | Makower |
| 7,849,860 B2 | 12/2010 | Makower et al. |
| 2001/0000041 A1 | 3/2001 | Selmon et al. |
| 2001/0012924 A1 | 8/2001 | Milo et al. |
| 2002/0103459 A1 | 8/2002 | Sparks et al. |
| 2002/0128677 A1 | 9/2002 | Duerig et al. |
| 2003/0023204 A1 | 1/2003 | Vo |
| 2003/0109809 A1 | 6/2003 | Jen et al. |
| 2003/0120195 A1 | 6/2003 | Milo et al. |
| 2003/0139763 A1 | 7/2003 | Duerig et al. |
| 2003/0208156 A1 | 11/2003 | Pham et al. |
| 2004/0133225 A1 | 7/2004 | Makower |
| 2004/0167554 A1 | 8/2004 | Simpson et al. |
| 2004/0230219 A1 | 11/2004 | Roucher |
| 2005/0038467 A1 | 2/2005 | Hebert |
| 2005/0171478 A1 | 8/2005 | Selmon et al. |
| 2006/0094930 A1 | 5/2006 | Sparks et al. |
| 2006/0184011 A1 | 8/2006 | Macaulay et al. |
| 2006/0276749 A1 | 12/2006 | Selmon et al. |
| 2007/0093779 A1 | 4/2007 | Kugler et al. |
| 2007/0093780 A1 | 4/2007 | Kugler et al. |
| 2007/0093781 A1 | 4/2007 | Kugler et al. |
| 2007/0093782 A1 | 4/2007 | Kugler et al. |
| 2007/0265596 A1 | 11/2007 | Jen et al. |
| 2008/0033423 A1 | 2/2008 | Peacock |
| 2008/0045996 A1 | 2/2008 | Makower et al. |
| 2008/0125748 A1 | 5/2008 | Patel |
| 2008/0125760 A1 | 5/2008 | Gilboa |
| 2008/0200896 A1 | 8/2008 | Shmulewitz |
| 2008/0228171 A1 | 9/2008 | Kugler et al. |
| 2008/0243065 A1 | 10/2008 | Rottenberg et al. |
| 2008/0243067 A1 | 10/2008 | Rottenberg et al. |
| 2008/0249397 A1 | 10/2008 | Kapadia |
| 2009/0005755 A1 | 1/2009 | Keith et al. |
| 2009/0088685 A1 | 4/2009 | Kugler et al. |
| 2009/0093791 A1 | 4/2009 | Heuser |
| 2009/0124899 A1 | 5/2009 | Jacobs et al. |
| 2009/0131785 A1 | 5/2009 | Lee et al. |
| 2009/0209910 A1 | 8/2009 | Kugler et al. |
| 2009/0264826 A1 | 10/2009 | Thompson |
| 2009/0292296 A1 | 11/2009 | Pansky et al. |
| 2009/0299171 A1 | 12/2009 | Duffy et al. |
| 2009/0299402 A1 | 12/2009 | Orihashi et al. |
| 2010/0063534 A1 | 3/2010 | Kugler et al. |
| 2010/0069945 A1 | 3/2010 | Olson et al. |
| 2010/0094259 A1 | 4/2010 | Makower et al. |
| 2010/0121357 A1 | 5/2010 | Flaherty et al. |
| 2010/0125244 A1 | 5/2010 | McAndrew |
| 2010/0324471 A1 | 12/2010 | Flaherty et al. |

OTHER PUBLICATIONS

Bolia, a. et al., "Recanalisation of Fermo-Popliteal Occlusions: Improving Success Rate by Subintimal Recanalisation", Journal of the Royal College of Radiologists, vol. 40 No. 3 May 1989, p. 325.

Bolia, A. et al., "Femoropopliteal and Crural Artery Recanalization Using Subintimal Angioplasty" Seminars in Vascular Surgery, vol. 8 No. 3, Sep. 1995, pp. 253-264.

Bolia, A. et al., "Percutaneous Transluminal Angioplasty of Occlusions of the Femoral and Popliteal Arteries by Subintimal Dissec-

(56) References Cited

OTHER PUBLICATIONS tion" CardioVascular and Interventional Radiology, vol. 13 No. 5, Oct./Nov. 1990, pp. 357-363.

Bolia, A., "Percuntaneous intentional extralumional (subintimal) recanalization of crural arteries" European Journal of Radiology, vol. 28 No. 2, Sep. 1998, pp. 199-204.

Bolia, Amman et al., "Percuntaneous Extraluminal (Subintimal) Recanalization of a Brachial Artery Occlusion Following Cardiac Catheterization" Cardiovascular Intervent Radiol, vol. 19, 1996, pp. 184-186.

Colombo, Antonio et al., "Treating Chronic Total Occlusions Using Subintimal Tracking and Reentry: The STAR Technique" Catheterizations and Cardiovascular Interventions, vol. 64, 2005, pp. 407-411.

Jacobs, Donald L. et al., "Crossing Chronic Total Occlusions of the Iliac and Femoral-Popliteal Vassels and the Use of True Lumen Reentry Devices" Perpectives in Vascular Surgery and Endovascular Therapy, AVolume 18 No. 1, 2006, pp. 31-37.

Kimura, Bruce J. et al., "Subintimal Wire Position During Angioplasty of a Chronic Total Coronary Occlusion: Detection and Subsequent Procedural Guidance by Intravascular Ultrasound" Catheterization and Cardiovascular Diagnosis, vol. 35 No. 3, Jul. 1995, pp. 262-265.

Nydahl, S., et al., "Technical Report: Recanalisation of All Three Infrapopliteal Arteries by Subintimal Angioplasty" Journal of the Royal College of Radiologists, vol. 51 No. 5, May 1996, pp. 366-367.

Rosenthal, E. et al., "Subintimal Dissection and False Tract Formation During Succesful Laser Thermal Probe ('Hot Tip') Angioplasty", Journal of Interventional Radiology, vol. 4 No. 1, 1989, pp. 19-22.

LUMEN REENTRY DEVICES AND METHODS

CROSS-REFERENCE TO RELATED APPLICATIONS

This application is a continuation of U.S. patent application Ser. No. 12/058,714, filed on Mar. 30, 2008, now U.S. Pat. No. 8,257,382, which claims priority to U.S. Provisional Patent Application 60/920,561, filed on Mar. 29, 2007, U.S. Provisional Patent Application 60/994,732, filed on Sep. 24, 2007, and U.S. Provisional Patent Application 60/997,099, filed on Oct. 2, 2007, the disclosures of which are incorporated herein by reference.

FIELD OF THE INVENTION

The present invention relates generally to devices and methods for reentry from one lumen into another lumen, such as but not limited to, reentry into a true lumen of a blood vessel from the extraluminal or sub-intimal space of the vessel.

BACKGROUND OF THE INVENTION

Chronic Total Occlusion (CTO) is an arterial vessel blockage (typically of plaque) that obstructs blood flow. CTO can occur both in coronary and peripheral arteries, and generally results from the same underlying cause—atherosclerosis.

One of the main difficulties in crossing a total occlusion is that the clinician does not know exactly how hard the plaque is until steering a guidewire to the occlusion. If the occlusion is relatively new, the plaque is likely to be soft enough and the guidewire may penetrate the plaque. However, after several weeks or months, the occlusion becomes fibrotic and calcified and the plaque becomes much harder, rendering guidewire crossing of the occlusion difficult if not impossible. Failure to cross the obstruction is the primary failure mode for CTO recanalization.

Another problem is that the CTO blocks contrast agents from flowing through the artery past the obstruction, preventing use of fluoroscopy to guide the guidewire. This increases the risk of perforating or dissecting the vessel, and may possibly increase the risk of tamponade—blood leaking out of the artery around the heart or peripheral organ. Even crossing a partially occluded blood vessel, especially long and curved occlusions, can be difficult and time consuming.

As is well known in anatomy, arteries generally have three coats or layers: an internal or endothelial coat (tunica intima of Kölliker); a middle or muscular coat (tunica media); and an external or connective-tissue coat (tunica adventitia). The two inner coats together are easily separated from the external adventitial layer, and the two inner coats are sometimes referred together as the intimal layer rather than the medial and intimal layers. It is known in the art that during an attempt to get past an occlusion with a guidewire, the guidewire sometimes inadvertently penetrates into the subintimal space between the intimal layer and the adventitial layer of the blood vessel as it attempts to cross the occlusion. Once in the subintimal space, it is very difficult and in many cases impossible to direct the guidewire back into the blood vessel true lumen beyond the occlusion.

However, techniques have been developed for entering the subintimal space on purpose and reentering the true lumen after the occlusion. This so-called subintimal recanalization can be a useful procedure, especially when using drug eluting stents, and is widely used. One of the advantages of subintimal recanalization is that a dissection of the subintimal space is more likely to produce a smooth lumen and improved blood flow than a lumen produced by plowing through calcified plaque. However, technical failure occurs in about 30% of patients undergoing percutaneous intentional extraluminal recanalization, mostly due to the inability to reenter the distal true lumen.

If during percutaneous extraluminal recanalization, the true lumen cannot be reentered with guidewire manipulation, a true lumen reentry device must be used. Currently there are two specially designed reentry devices in the market.

The Pioneer reentry catheter (from Medtronic, Santa Rosa, Calif., US) is a 7 Fr. intravascular ultrasound (IVUS) device that is placed in the dissection beyond the occlusion. The IVUS image provides an image of the vessel wall. The catheter is constructed with a monorail lumen for delivery of the device over a 0.014 inch wire, and a second wire lumen through the end of the catheter, which ends in a curved nitinol needle that can retract into the catheter near the distal end. The needle is deployed by sliding it out of a distal port at the side of the catheter just proximal to the IVUS transducer. The IVUS device is used to ultrasonically guide, turn and manipulate the curved needle to arrive at the correct radial orientation for reentry into the true lumen.

The Outback LTD reentry catheter (Cordis, Miami Lakes, Fla., US) is a 6 Fr. catheter with a retractable nitinol curved needle at the distal end. The needle is straight when withdrawn in the catheter. When pushed forward, the needle is restored to its curved shape and can penetrate the medial and intimal layers to reenter the true lumen. The rotational orientation of needle deployment is provided by fluoroscopic guiding markers on the catheter.

SUMMARY OF THE INVENTION

The present invention seeks to provide novel devices and methods for lumen reentry, as is described more in detail hereinbelow.

The present invention has many applications, such as but not limited to, true lumen reentry in PTA (percutaneous transluminal angioplasty), PTCA (percutaneous transluminal coronary angioplasty), and any other percutaneous or non-percutaneous placement of a catheter between two adjacent layers of vessels, arteries, soft tissue, or any other human tissue.

In one embodiment of the invention, a device and method are provided for reentry into a true lumen of a blood vessel from the extraluminal or sub-intimal space of the vessel. The invention eliminates the need for rotational direction by an imaging system or for curved needles as in the prior art. Instead, in one embodiment of the invention that includes a catheter and guidewire, the lumen reentry device automatically bends the catheter after the occlusion so that the catheter distal end is directed in the direction of the true lumen so that the guidewire can penetrate back into the true lumen.

The invention assists the clinician (e.g., cardiologist, radiologist, vascular surgeons or any other medical doctor who engages in angioplasty procedures) in treating total occlusions, and can be used to cross both new and soft plaque and old and hard plaque.

In one non-limiting embodiment of the invention, the method includes 1) inserting a guidewire in a balloon catheter into the proximal vessel true lumen, 2) dissecting the vessel with the guidewire near the proximal end of the occlusion, 3) moving the guidewire through the subintimal space of the blood vessel distally past the occlusion, 4) moving the balloon catheter distally past the occlusion over the guidewire, 5) moving the guidewire proximally to the balloon, and deploying (inflating) a balloon that deflects the intimal layer away from the adventitial layer of the blood vessel and bends the catheter towards the inner volume of the true lumen; and 6) penetrating the intimal layer back into the true lumen and reentering the true lumen with the guidewire. The method may further include performing balloon angioplasty through the recanalized lumen, and deploying a stent. The stent is typically long enough to start in the proximal true lumen and end in the distal true lumen.

There is provided in accordance with an embodiment of the invention a lumen reentry device including a catheter including a balloon disposed at a distal end thereof, the catheter being formed with a first lumen through the balloon for passing therethrough a guidewire and a second lumen for inflation and deflation of the balloon, the catheter and the balloon being sized and shaped for entry between two layers of a wall of a body lumen, wherein upon expansion of the balloon when placed between the layers, a distal portion of the first lumen that passes through the balloon is bent with respect to a portion of the first lumen proximal to the balloon and is directed towards the body lumen. The balloon may include an inverted distal neck.

In one non-limiting embodiment of the invention, a guidewire passes through the first lumen and is adapted to pierce at least one of the layers to enter the body lumen. It is noted that the "guidewire" piercing the layer or layers encompasses not just the guidewire but any stylet, needle or wire capable of puncturing through to the lumen.

In another non-limiting embodiment of the invention, a hypo-tube needle is disposed in the first lumen and a guidewire passes through an internal cavity of the needle, a distal end of the needle being adapted to pierce at least one of the layers to enter the body lumen.

In one non-limiting embodiment of the invention, a diameter of the balloon is not more than a diameter of the body lumen.

In one non-limiting embodiment of the invention, a length of the balloon is not more than the diameter of the balloon. Alternatively, the length of the balloon can be double the diameter of the balloon. Other lengths are also possible.

In one non-limiting embodiment of the invention, the catheter is formed with a pivoting portion proximal to the distal portion upon which the balloon is disposed. The pivoting portion may include a weakened section having a smaller wall thickness than other portions of the catheter. Alternatively, the pivoting portion includes a portion made of a flexible material. Alternatively, the pivoting portion includes a joint. Alternatively, the pivoting portion includes a section which is softer and easier to bend than the rest of the catheter.

In one non-limiting embodiment of the invention, the catheter is slidingly disposed in a sheath and the distal portion of the catheter is bendable at a juncture with a distal end of the sheath.

In one non-limiting embodiment of the invention, a diameter of the balloon is equal to or slightly larger than a diameter of the body lumen.

In one non-limiting embodiment of the invention, the device further includes a second balloon mounted on the catheter proximal to the balloon, the second balloon being inflatable through a third lumen formed in the catheter.

It is noted that the invention is not limited in the number of balloons and lumens. For example, the device can include four lumens (two for inflating balloons, one for passing a guidewire, and another one for injecting a contrast agent). Another example is a three lumen device (one for inflating a balloon, one for passing a guidewire, and one for injecting a contrast agent).

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
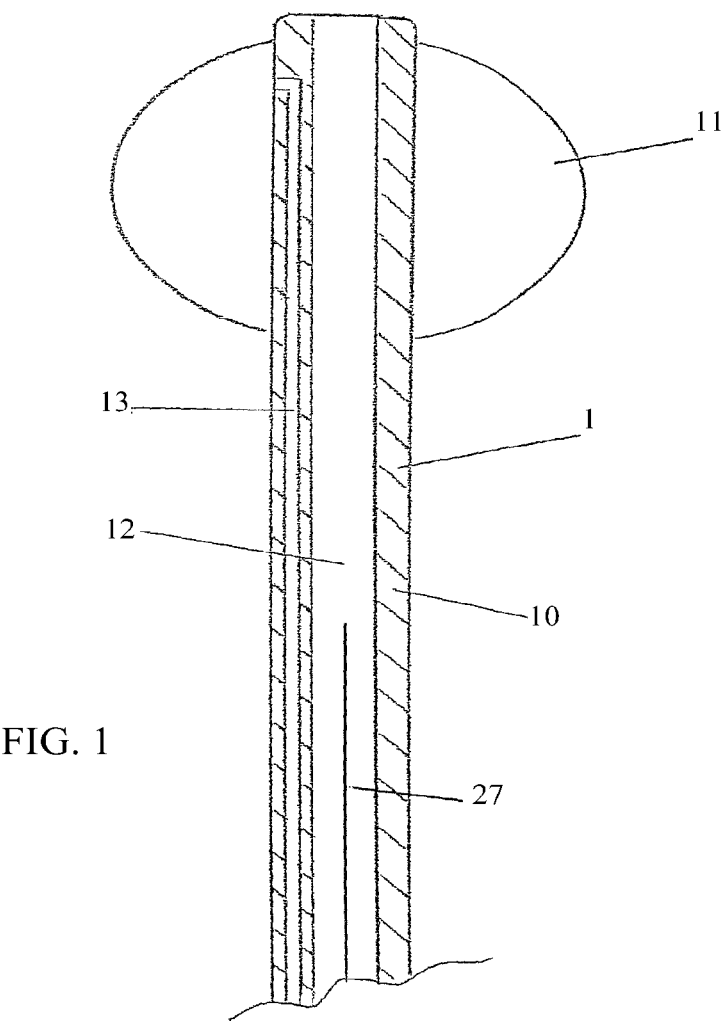
FIG. 1 is a simplified, partially sectional, schematic illustration of a lumen reentry device, constructed and operative in accordance with an embodiment of the present invention.

Reference is now made to FIG. 1, which illustrates a lumen reentry device 1, constructed and operative in accordance with an embodiment of the present invention. Device 1 includes a catheter 10 which has a balloon 11 disposed at a distal end thereof. The distal end of catheter 10 protrudes only slightly, or does not protrude at all, beyond balloon 11. The significance of this will be explained further below. Catheter 10 is formed with a first lumen 12 through balloon 11 for passing therethrough a guidewire 27, and a second lumen 13 for inflation and deflation of balloon 11.

Catheter 10 may be fabricated from polyethylene, polyurethane, PEBAX (polyether block amide from Arkema), nylon or other polymers known in the art. The catheter shaft can also be made from polymers reinforced with metal wires braid or springs, as is known in the art.

Balloon 11 may be fabricated from polyurethane, silicon, PET (polyethylene terephthalate), and other suitable polymers known in the art.

Figure 3:
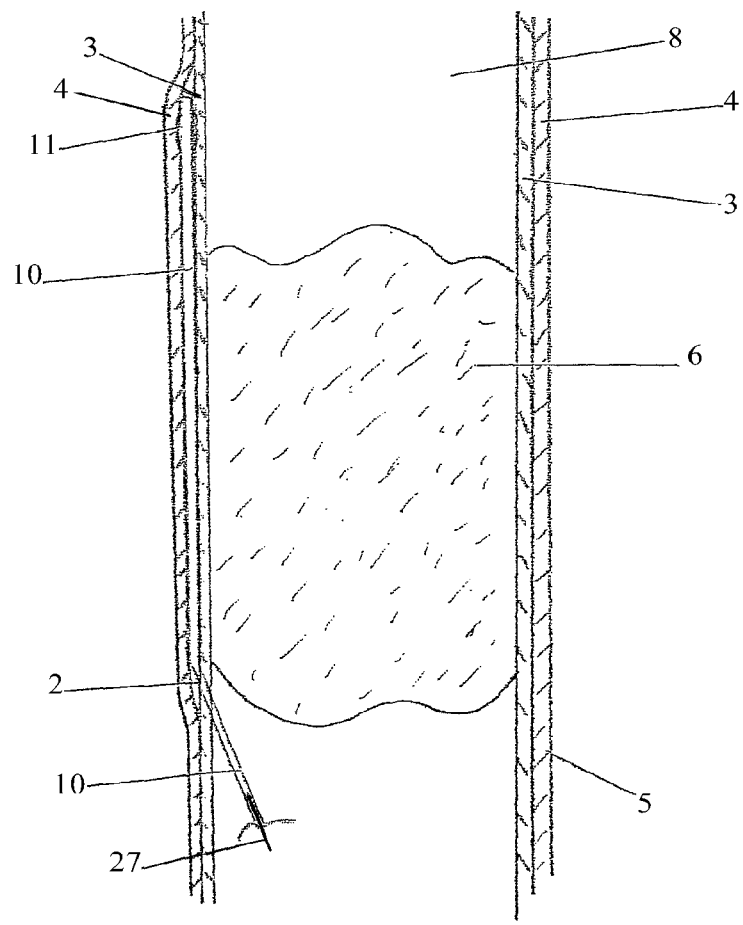
FIGS. 3 and 4 are simplified, partially sectional, schematic illustrations of the lumen reentry device of FIG. 1 introduced in a blood vessel subintimal space, in accordance with an embodiment of the present invention, respectively before and after balloon inflation.

Reference is now made to FIG. 3, which illustrates lumen reentry device 1 introduced in a true lumen 8 and then through a dissection 2, typically between an internal intimal layer 3 (perhaps both the medial layer together with the intimal layer) and an external adventitial layer 4 of a blood vessel 5, over a guidewire 27 (shown for clarity only at the proximal end of catheter 10). Balloon 11 has been passed beyond the distal end of an occlusion 6.

In the illustrated embodiment, balloon 11 is a small conical balloon. The balloon diameter is preferably similar or smaller than the diameter of the true lumen 8 of blood vessel 5. Balloon 11 can also have a round ball (spherical) shape or other similar elliptical shapes, wherein its diameter is a few times the diameter of catheter 10, but not more than the diameter of true lumen 8. In the illustrated embodiment, the length of balloon 11 is relative short compared to common angioplasty balloons, usually not more than twice its diameter.

Figure 4:
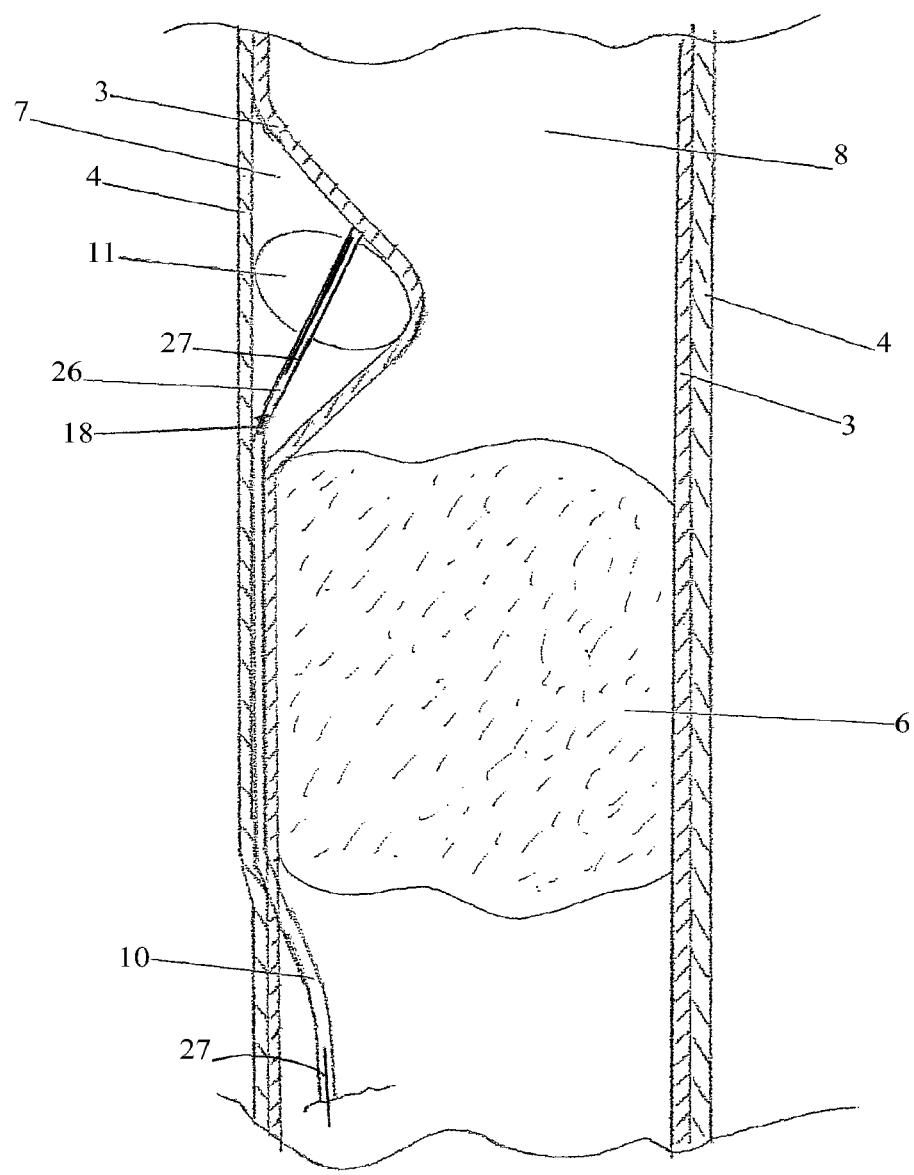

When catheter 10 and balloon 11 are in place as shown in FIG. 3, balloon 11 is then inflated, e.g., to a pressure of several atmospheres, as shown in FIG. 4. The balloon inflation creates a space 7 (void or passageway) by pushing the surrounding tissues, that is, intimal layer 3 and external adventitial layer 4. Balloon 11 is located subintimally between layers 3 and 4, and the high pressure inflation produces a relatively high force on the two tissue layers 3 and 4. The forces cause the internal intimal layer 3 to yield first, bending or folding towards the adjacent true lumen 8, rather than causing the external adventitial layer 4 to stretch or become extended. This is because the force needed to stretch the tougher external adventitial layer 4 is much higher than the force needed to fold or bend the more flexible internal intimal layer 3, especially since the internal intimal layer 3 is folding toward the true lumen 8.

Folding of the internal intimal layer 3, with minimal or no movement from the external adventitial layer 4, causes the distal end of catheter 10 to bend towards the true lumen 8. This automatically points the distal end of catheter 10 and guidewire 27 (shown also at the distal end of catheter 10 in FIG. 4) correctly towards the true lumen 8 for punching back through the internal intimal layer 3 into the true lumen 8, without any need for an imaging system for rotational orientation.

The penetration into the true lumen 8 through the internal blood vessel layer 3 can be done simply and directly with guidewire 27. Afterwards catheter 10 can be withdrawn from the patient to leave guidewire 27 in place, such as for placing a stent (not shown). It is noted that the same guidewire 27 can be used for catheter 10 and for introducing the stent, which significantly facilitates the clinician's work.

Figure 2:
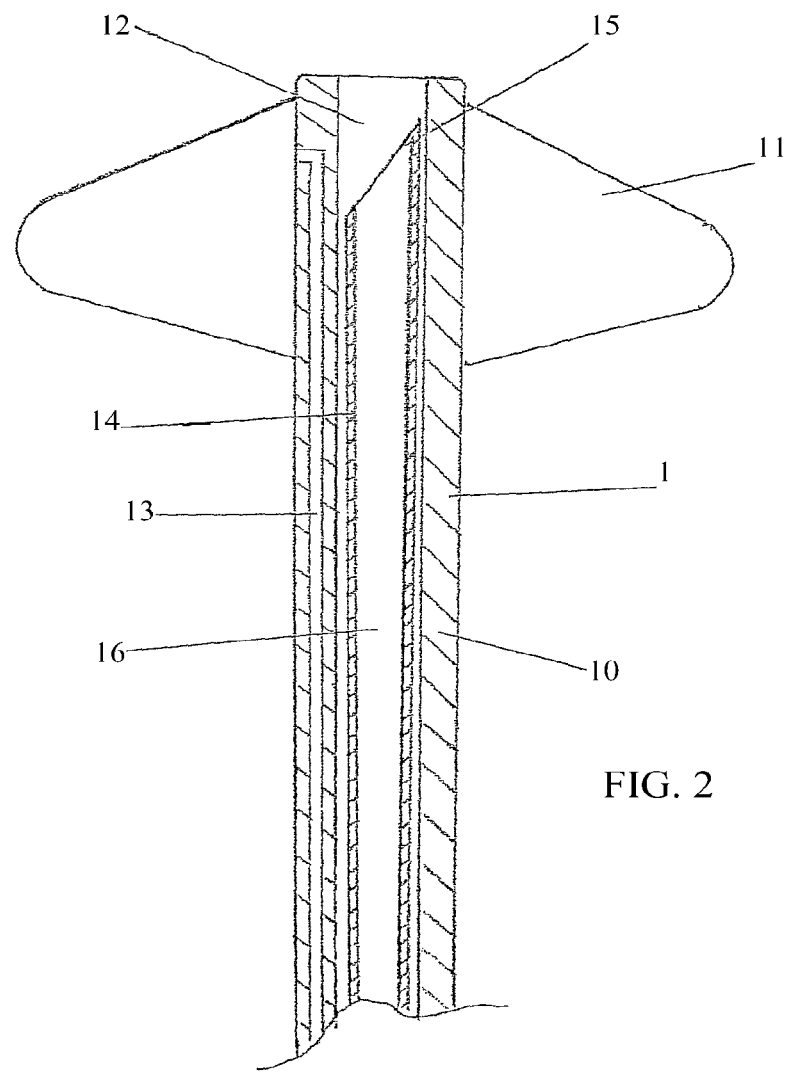
FIG. 2 is another simplified, partially sectional, schematic illustration of the lumen reentry device of FIG. 1, including a hypo-tube needle disposed in a catheter.

Reference is now made to FIG. 2, which illustrates an alternative way of puncturing the internal layer 3 for reentry into the true lumen 8. In this embodiment, a flexible hypo-tube needle 14 is disposed in first lumen 12 of catheter 10. Hypo-tube 14, preferably made from a shape memory alloy such as nitinol, may be pre-cut to a needle shape at its distal end 15.

The embodiment of FIG. 2 is used the same way as the embodiment of FIG. 1, except that in the embodiment of FIG. 2, after balloon inflation, hypo-tube needle 14 is used to puncture internal intimal layer 3 to penetrate back into the true lumen 8. Guidewire 27 may then be introduced through an internal cavity 16 of needle 14 into the true lumen 8. Afterwards needle 14 may be retracted into catheter 10, and catheter 10 may be withdrawn from the patient, leaving guidewire 27 in place, as described above. The bending angle is a function of the catheter point of bending at the plaque distal end and the balloon diameter.

As mentioned above, the distal end of catheter 10 protrudes only slightly, or does not protrude at all, beyond balloon 11. The significance of this is now explained with reference to FIGS. 7A-8.

Figure 7A:
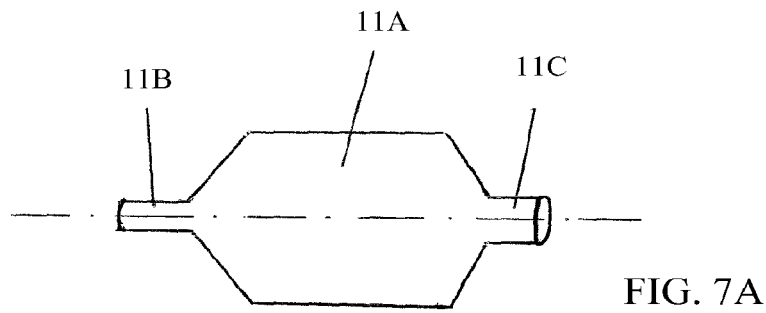
FIGS. 7A and 7B are simplified schematic illustrations of a non-inverted distal balloon neck (FIG. 7A) and a balloon with such a neck mounted on a catheter (FIG. 7B).
Figure 7B:
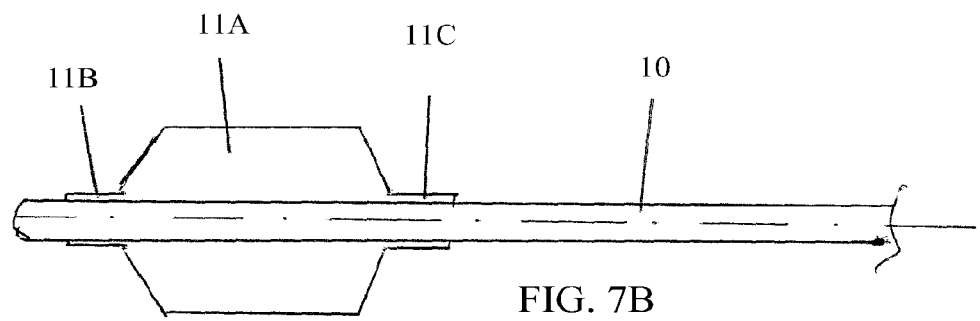

FIGS. 7A and 7B illustrate a balloon having a balloon body 11A and non-inverted distal and proximal necks 11B and 11C, respectively. FIG. 7B shows such a balloon mounted on catheter 10.

Figure 7C:
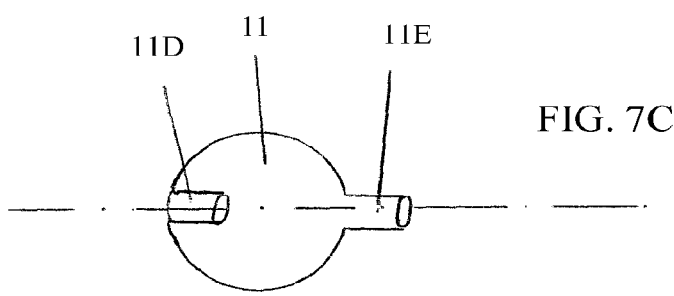
FIGS. 7C and 7D are simplified schematic illustrations of an inverted distal balloon neck (FIG. 7C) and a balloon with such a neck mounted on a catheter (FIG. 7D), in accordance with an embodiment of the present invention.
Figure 7D:
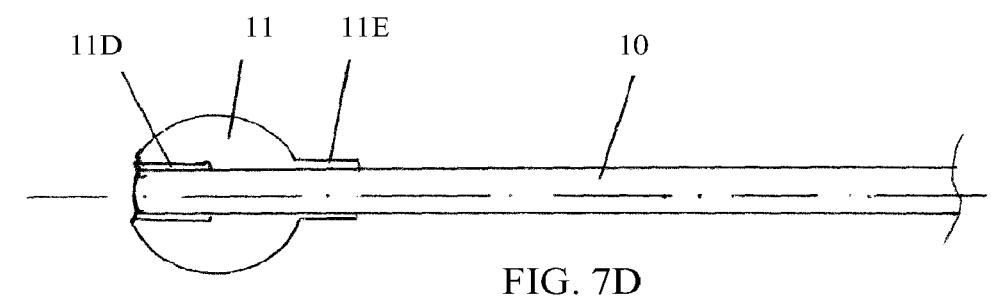

In contrast, FIGS. 7C and 7D illustrate the balloon 11 of the present invention with distal and proximal necks 11D and 11E, respectively. Distal neck 11D is inverted into the inner space of balloon 11. The inverse or inverted distal neck 11D of balloon 11 can be manufactured directly as an inverted neck or can be made non-inverted and then inverted before bonding to catheter 10. Proximal neck 11E can be made and bonded in a standard way.

Figure 8:
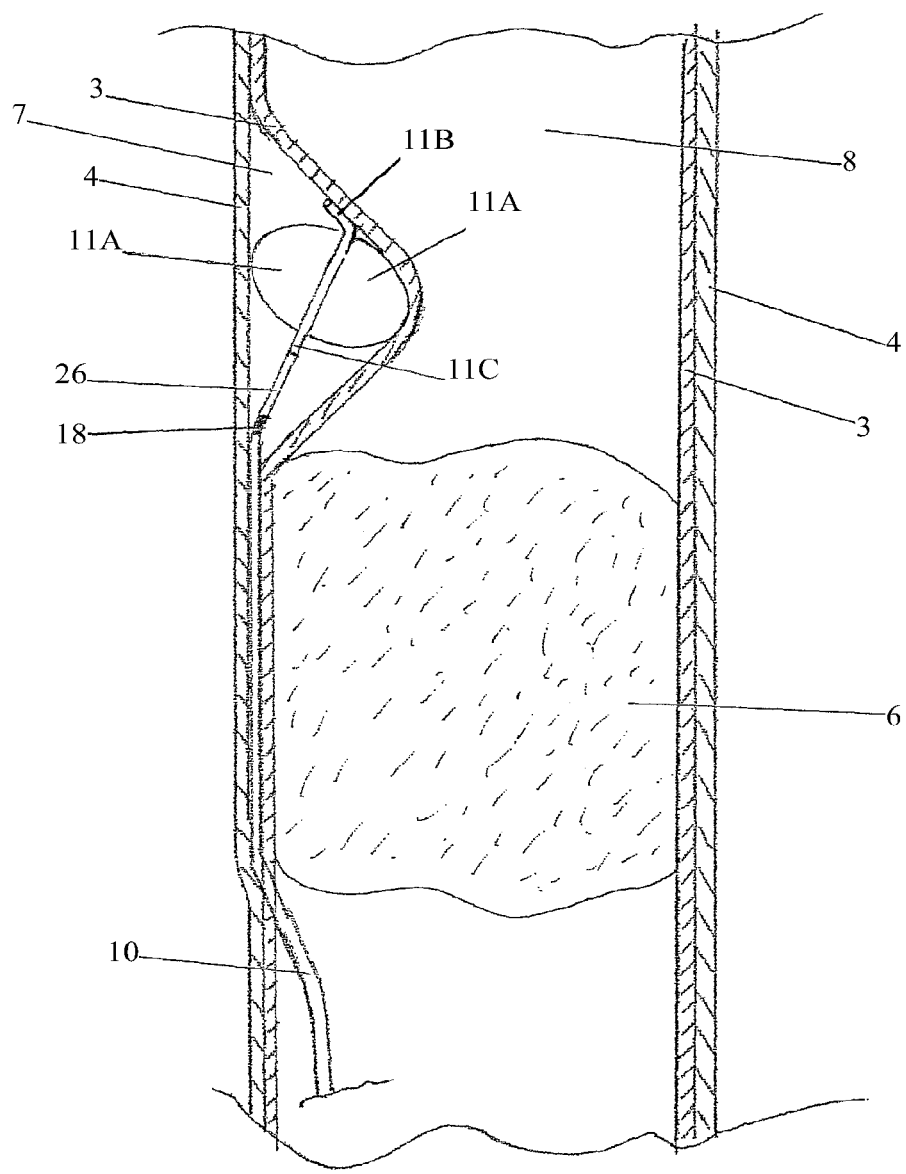
FIG. 8 is a simplified, partially sectional, schematic illustration of a lumen reentry device in the subintimal space of a blood vessel after balloon inflation, showing that if the balloon has a protruded, non-inverted distal neck it may fail to orient the device properly for puncturing the blood vessel for reentry into the true lumen.

Reference is now made to FIG. 8, which illustrates the lumen reentry device with a balloon having the non-inverted distal neck 11A in the subintimal space of a blood vessel after balloon inflation. It is seen that the non-inverted distal neck 11A can bend and point away from the true lumen 8, thereby failing to orient the device properly for puncturing the blood vessel for reentry into the true lumen 8.

Reference is made again to FIG. 4. In another embodiment of the present invention, catheter 10 may be formed with a pivoting portion 18 proximal to a distal portion 26 of catheter 10 upon which balloon 11 is disposed. Pivoting portion 18 may be formed in several ways. For example, pivoting portion 18 may comprise a weakened section having a smaller wall thickness, or a portion made of a flexible material, or a joint, or a section without metal wires, springs or braids, making it softer and easy to bend or rotate with minimal resistance from the rest of the catheter shaft. The position of pivoting portion 18, together with the balloon diameter, defines the catheter distal end bend angle.

Figure 5:
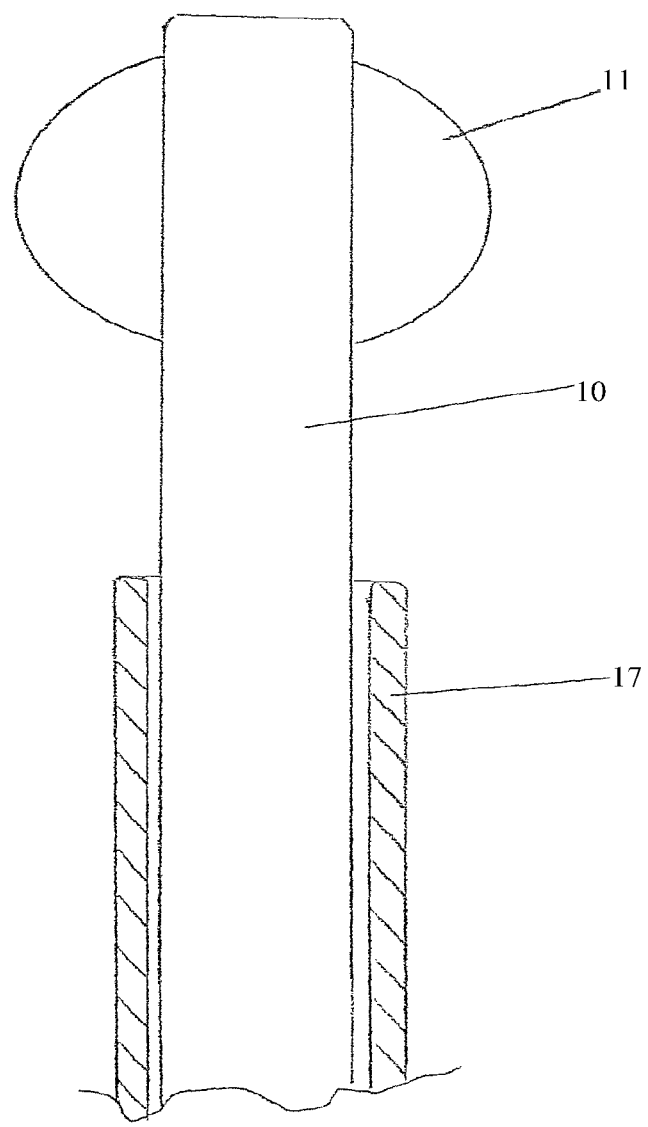
FIG. 5 is a simplified, partially sectional, schematic illustration of a lumen reentry device with a covering sheath, constructed and operative in accordance with another embodiment of the present invention.
Figure 6:
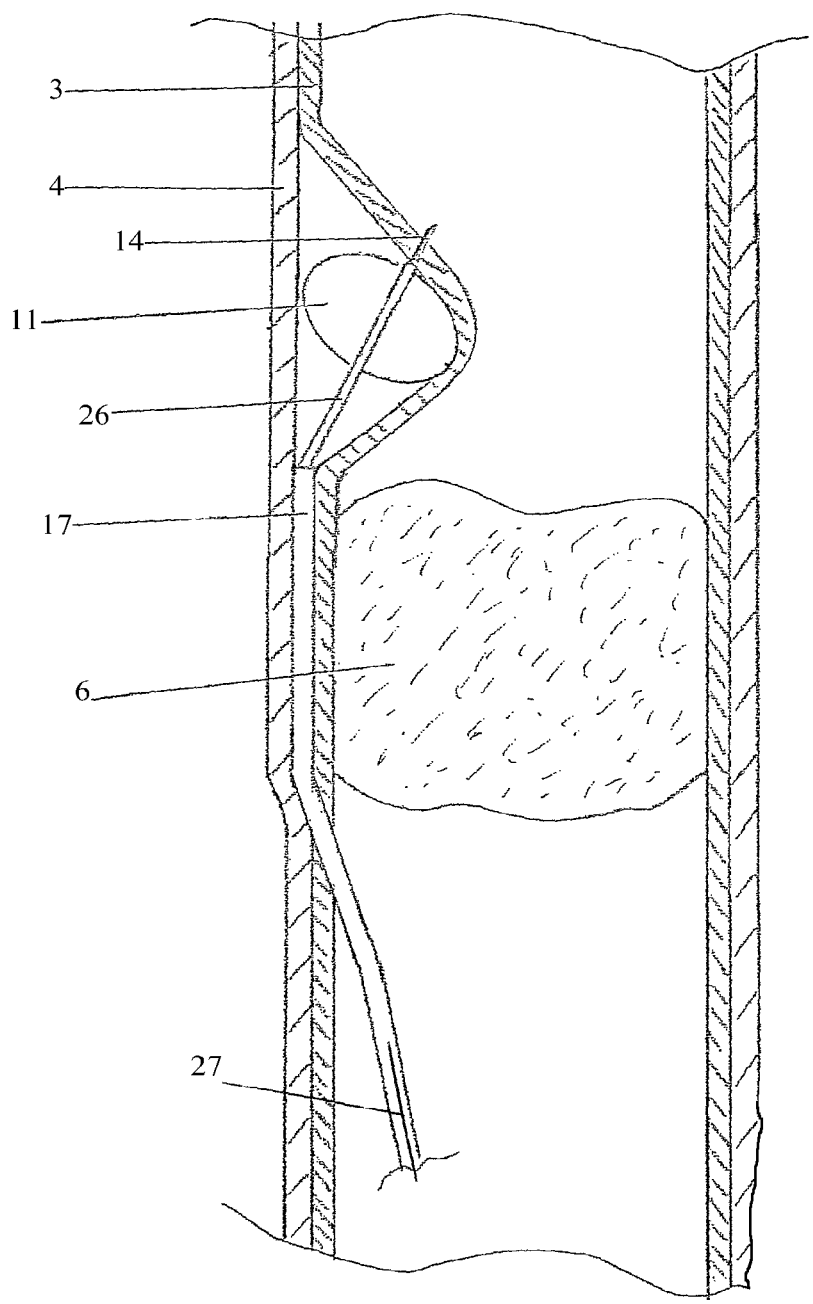
FIG. 6 is a simplified, partially sectional, schematic illustration of the lumen reentry device of FIG. 5 introduced in the subintimal space of a blood vessel, with a hypo-tube penetrating through the internal blood vessel wall layer, after moving the covering sheath proximally backwards and after balloon inflation.

Reference is now made to FIGS. 5 and 6, which illustrate lumen reentry device 1 with a covering sheath 17, constructed and operative in accordance with another embodiment of the present invention. Sheath 17 may be fabricated from polyurethane, PET, PTFE or other suitable polymers known in the art. As seen in FIG. 6, catheter 10 and sheath 17 are inserted together over guidewire 27. After being placed distally beyond occlusion 6, sheath 17 can be pulled slightly backwards (proximally) to a pre-determined distance and distal portion 26 of catheter 10 bends at the juncture with the distal end of sheath 17. The bending angle is a function of the catheter point of bending at the sheath distal end and the balloon diameter.

Figure 9:
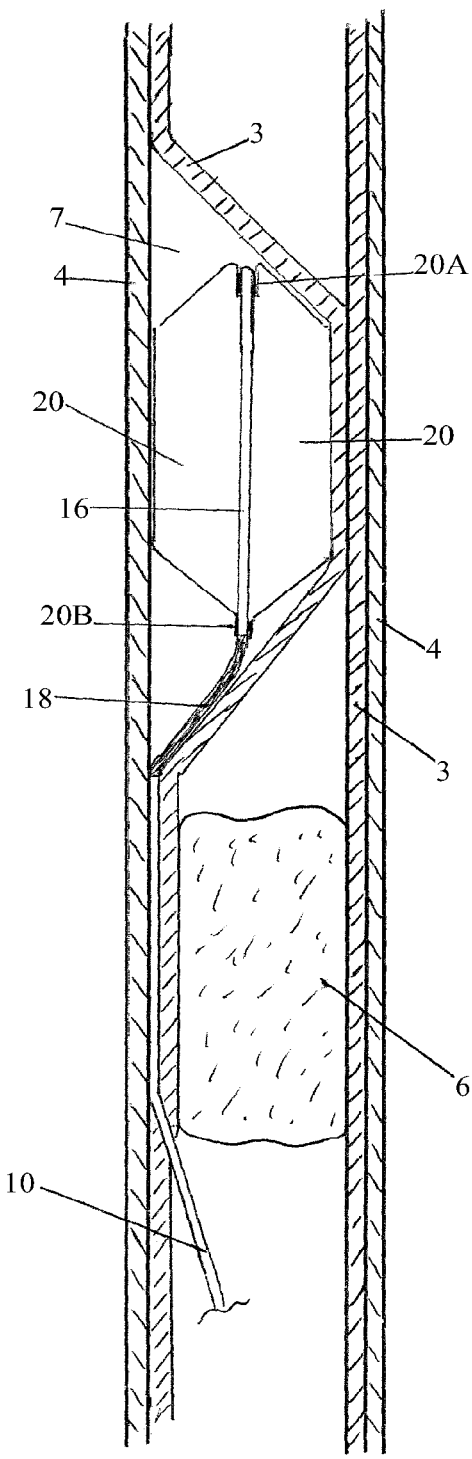
FIG. 9 is a simplified, partially sectional, schematic illustration of a lumen reentry device, constructed and operative in accordance with yet another embodiment of the present invention, introduced in the subintimal space of a blood vessel, using a long angioplasty balloon having an inverted distal neck and no neck distal protrusion.

Reference is now made to FIG. 9, which illustrates a lumen reentry device, constructed and operative in accordance with yet another embodiment of the present invention. In this embodiment, a long balloon 20, similar to balloons used in angioplasty procedures, but having inverted distal neck 20A as described before, can be used for reentry. Proximal neck 20B can be non-inverted as described before. If the diameter of balloon 20 is equal to or slightly larger than the blood vessel internal diameter, expansion of balloon 20 forces the internal layer 3 to fully collapse towards the opposite blood vessel wall. A guidewire or straight needle can then be used to punch the blood vessel internal layer 3 into the true lumen 8, as described above. Pivoting portion 18 of catheter 10 can be used proximally to balloon 20 to allow rotating or bending balloon 20.

Figure 10:
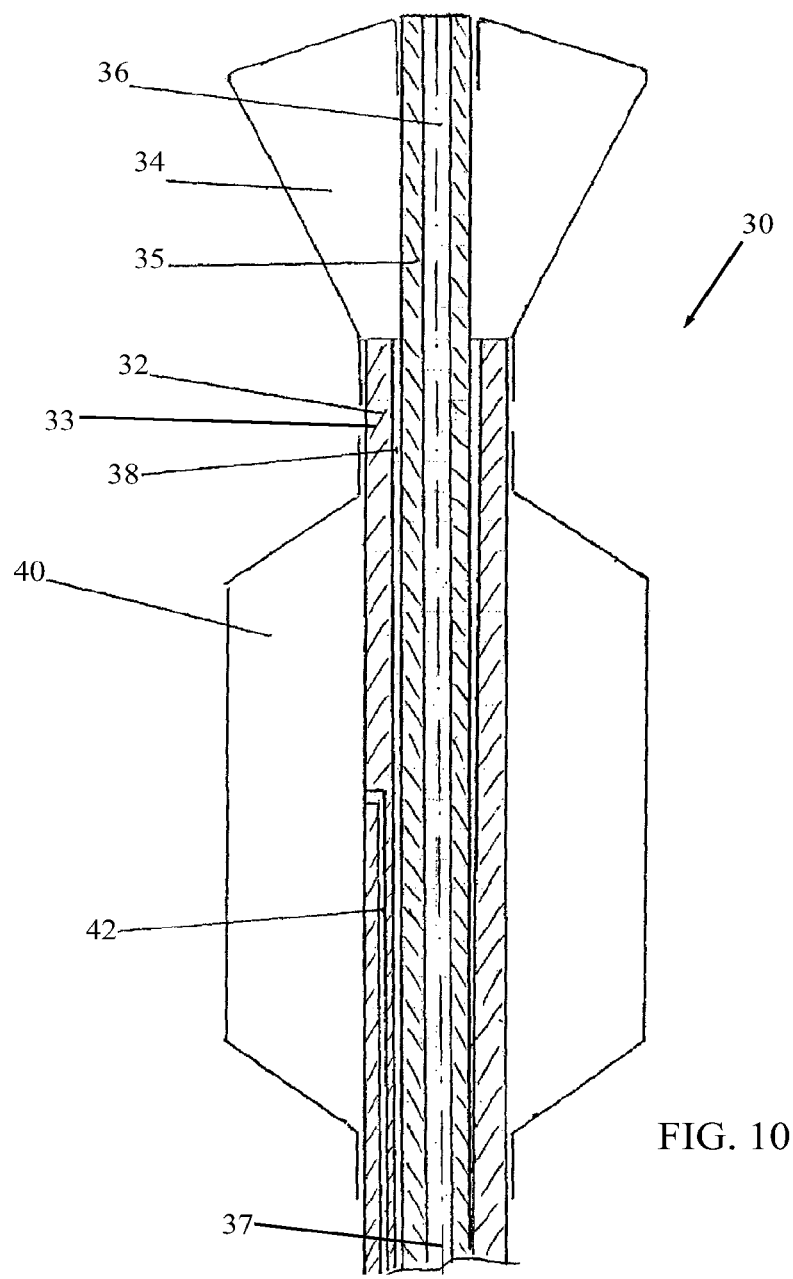
FIG. 10 is a simplified, partially sectional, schematic illustration of a lumen reentry device, constructed and operative in accordance with still another embodiment of the present invention, and including a reentry balloon and a PTA balloon on the same catheter.

Reference is now made to FIG. 10, which illustrates a lumen reentry device 30, constructed and operative in accordance with still another embodiment of the present invention.

Device 30 includes a catheter 32 which has a balloon 34 disposed at a distal end thereof. The distal end of catheter 32 protrudes only slightly, or does not protrude at all, beyond balloon 34, as in the previous embodiments. Accordingly the distal neck of balloon 34 is inverted. Catheter 32 includes an external tube 33 in which an internal tube 35 is disposed. The distal neck of balloon 34 may be bonded or otherwise attached to internal tube 35, and its proximal neck to external tube 33. Internal tube 35 is smaller, and preferably softer or more flexible than external tube 33, thereby creating a pivotal point for balloon 34 to bend when inflated. Internal tube 35 is formed with a first lumen 36 for passing therethrough a guidewire 37. A second lumen 38 is formed between the internal and external tubes 35 and 33 for inflation and deflation of balloon 34.

Balloon 34 is a reentry balloon and its use is as described above. In addition, proximal to balloon 34, a second balloon 40 is mounted on the same catheter 32. Second balloon 40 is a PTA balloon and may be attached to the external tube 33 of catheter 32 with regular, non-inverted necks. Second balloon 40 may be inflated or deflated via a third lumen 42 formed in the external tube 33 of catheter 32.

Figure 11:
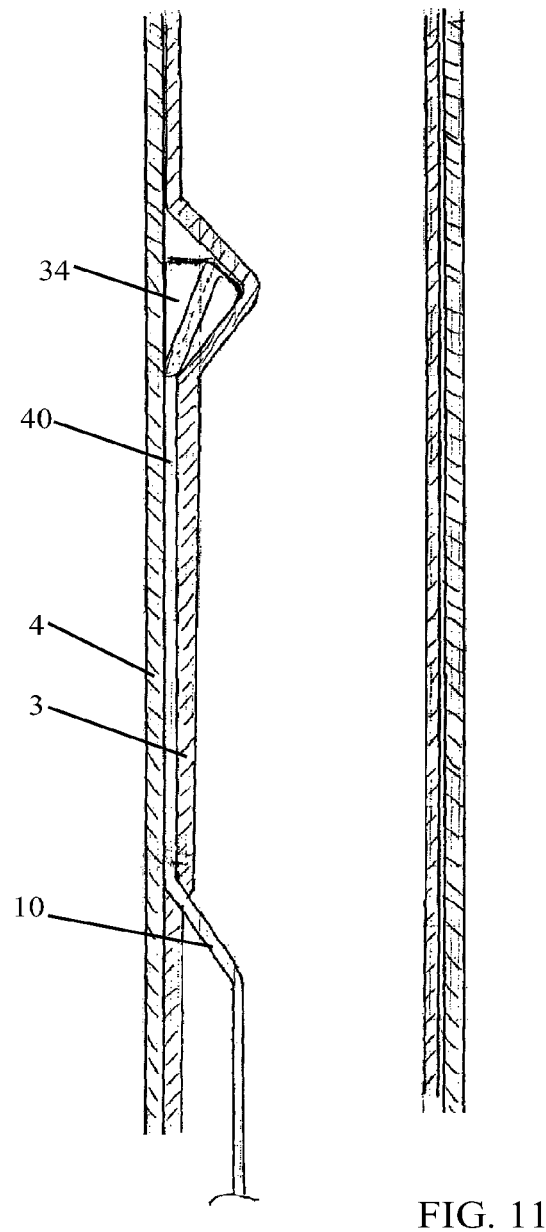
FIG. 11 is a simplified, partially sectional, schematic illustration of the lumen reentry device of FIG. 10 introduced in the subintimal space of a blood vessel, and after balloon inflation.

Reference is now made to FIG. 11, which illustrates lumen reentry device 30 introduced in the subintimal space of a blood vessel, and after balloon inflation. The conical shape of balloon 34 helps direct the distal end of catheter 32 towards the true lumen. The second balloon 40 may then be inflated for angioplasty and stent introduction procedures.

Other variations of the embodiment of device 30 are in the scope of the invention. For example, the device may include two lumens (one for the guidewire and another for the balloon), wherein the balloon lumen can inflate either two separate balloons (PTA and reentry) or one balloon that has two sub-balloons (two "humps"), one for PTA and the other for reentry.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed:

1. A balloon catheter for placement between first and second tissue layers of a wall of a blood vessel, the balloon catheter comprising:
   a catheter shaft including an outer tubular member and an inner tubular member extending through the outer tubular member; and
   a conically shaped balloon having a proximal balloon neck secured to the outer tubular member and an inverted distal balloon neck secured to the inner tubular member;
   the conically shaped balloon has a proximal portion tapering radially outward in a distal direction from the proximal balloon neck, and the conically shaped balloon has a distal portion tapering radially outward in a proximal direction from the distal balloon neck, the proximal portion and the distal portion converging at an outermost radial extent of the conically shaped balloon;
   wherein in an inflated state the conically shaped balloon has an overall length measured from the proximal balloon neck to the distal balloon neck and a outermost diameter measured at the outermost radial extent, the overall length being less than the outermost diameter.

2. The balloon catheter of claim 1, wherein the proximal portion has a first length and the distal portion has a second length, wherein the first length is greater than the second length.

3. The balloon catheter of claim 2, wherein the first length is less than the outermost diameter of the balloon.

4. The balloon catheter of claim 1, wherein the proximal portion has a first length and the distal portion has a second length, wherein the first length is less than the outermost diameter of the balloon.

5. The balloon catheter of claim 1, wherein the distal end of the inner tubular member does not protrude distally beyond the conically shaped balloon.

6. The balloon catheter of claim 1, wherein the distal end of the inner tubular member protrudes only slightly beyond the conically shaped balloon.

7. The balloon catheter of claim 1, wherein the proximal balloon neck is secured to a distal end of the outer tubular member.

8. The balloon catheter of claim 1, wherein the inverted distal balloon neck is secured to a distal end of the inner tubular member.

9. The balloon catheter of claim 1, wherein a distal portion of the catheter shaft is configured to bend with respect to a proximal portion of the catheter shaft upon expansion of the conically shaped balloon between the first and second tissue layers.

10. The balloon catheter of claim 1, wherein the catheter shaft includes a guidewire lumen defined by the inner tubular member for passage of a guidewire therethrough.

11. The balloon catheter of claim 1, wherein the catheter shaft includes an inflation lumen defined between the inner tubular member and the outer tubular member in fluid communication with the conically shaped balloon.

12. A subintimal re-entry balloon catheter for placement between first and second tissue layers of a wall of a blood vessel to redirect a penetration member into a lumen of the blood vessel, the balloon catheter comprising:
    an elongate shaft including an inner tubular member having a guidewire lumen extending therethrough and an outer tubular member surrounding the inner tubular member and defining an inflation lumen between the inner tubular member and the outer tubular member; and
    a conically shaped balloon mounted on a distal portion of the elongate shaft, the conically shaped balloon having a proximal balloon neck secured to a distal end of the outer tubular member and an inverted distal balloon neck secured to a distal end of the inner tubular member;
    the conically shaped balloon having a proximal portion tapering radially outward in a distal direction from the proximal balloon neck to an outermost radial extent of the balloon and a distal portion tapering radially outward in a proximal direction from the distal balloon neck to the outermost radial extent of the balloon;
    wherein in an inflated state the conically shaped balloon has an overall length measured from the proximal balloon neck to the distal balloon neck and a outermost diameter measured at the outermost radial extent, the overall length being less than the outermost diameter; and wherein the conically shaped balloon is configured such that the distal portion of the elongate shaft is bent relative to a portion of the elongate shaft proximal of the conically shaped balloon when the conically shaped balloon is in the inflated state between the first and second tissue layers such that a distal opening of the guidewire lumen is oriented toward the lumen of the blood vessel.

* * * * *